US006213963B1

(12) United States Patent
Smith

(10) Patent No.: US 6,213,963 B1
(45) Date of Patent: Apr. 10, 2001

(54) APPARATUS FOR THE MASSAGING OF TOES

(76) Inventor: Gregory D. Smith, 3804 Johnson St., Ft. Smith, AR (US) 72904

( * ) Notice: Subject to any disclaimer, the term of this patent is extended or adjusted under 35 U.S.C. 154(b) by 0 days.

(21) Appl. No.: 09/293,375

(22) Filed: Apr. 16, 1999

Related U.S. Application Data

(60) Provisional application No. 60/082,010, filed on Apr. 16, 1998.

(51) Int. Cl.[7] ........................ A61M 7/00

(52) U.S. Cl. ........................ 601/104; 601/101; 601/103; 601/97

(58) Field of Search ........................ 601/112, 111, 601/116, 85, 87, 89, 93, 95, 97, 101, 103, 104, 107, 108, 109, 134–137; 15/21.1, 32, 33, 34, 35, 36, 37, 38; 607/79

(56) References Cited

U.S. PATENT DOCUMENTS

D. 157,306 12/1950 Vogt .
1,623,124 * 4/1927 Laufe ........................ 601/135
2,424,509 * 7/1947 Singer ........................ 15/21.1
3,499,439 3/1970 Boller .
3,529,593 * 9/1970 Perry ........................ 601/114
3,716,048 2/1973 Alonso .
3,810,463 * 5/1974 Krumenacher ........................ 601/114
3,939,825 * 2/1976 Krummenacher ........................ 601/104
4,506,659 * 3/1985 Chester ........................ 601/97
4,807,602 2/1989 Scarborough et al. .
5,447,491 9/1995 Bellandi ........................ 601/112
5,729,858 * 3/1998 Riffel ........................ 15/160

FOREIGN PATENT DOCUMENTS

3926256 * 2/1991 (DE) ........................ 601/104

* cited by examiner

*Primary Examiner*—Justine R. Yu
(74) *Attorney, Agent, or Firm*—Brent A. Capehart; Fellers, Snider, Blankenship, Bailey & Tippens

(57) ABSTRACT

An apparatus for massaging toes having a plurality of massaging fingers which provide the massaging effect on and between the toes of a user. The massaging fingers are powered by a drive mechanism means, such as an electric motor and a motion transfer apparatus.

9 Claims, 4 Drawing Sheets

APPARATUS FOR THE MASSAGING OF TOES

CROSS-REFERENCE TO RELATED APPLICATIONS

This application claims the benefit of and incorporates by reference prior filed Provisional Application Ser. No. 60/082,010 filed Apr. 16, 1998 entitled "Toe Massager".

BACKGROUND OF THE INVENTION

1. Field of the Invention.

The present invention relates to a foot massage device operated by a drive means such as an electric and/or battery powered motor. More specifically, the present invention relates to a foot message device having a plurality massaging fingers providing a massaging effect to the toe of a user.

2. Prior Art.

The prior art disclosed various types of massagers. Typical examples of such massagers are exemplified in the disclosures of U.S. Pat. No. 4,807,602 issued to Scarborough on Feb. 28, 1989 which discloses a hydro-massaging device, U.S. Pat. No. D157,306 issued to Vogt on Feb. 14, 1950 which discloses an electrical foot vibrator, U.S. Pat. No. 5,447,491 issued to Bellandi on Sep. 5, 1995 which discloses an anticellulitis massaging device operated by an electric motor and U.S. Pat. No. 3,499,439 issued to Boller on May 26, 1967 which discloses a hand-held massaging device utilizing inner mesh gears carrying one or more massaging implements.

As the prior art above demonstrates these devices are suited for their intended purposes, however, nothing in any prior art discloses a device which is suited for the purpose for providing a massaging effect on and between the toes of a foot.

SUMMARY OF THE INVENTION

The present invention generally relates to a foot massaging device, in particular to a device which is able to provide a massaging effect between the toes of a foot which utilizes the plurality of massaging fingers.

The massaging fingers provide a massaging effect to the toes of the user. The primary embodiment of the invention envisions a device which is used on a single foot. However, alternative embodiments envision the device configured in such a manner at to be able to provide a massaging effect to both feet of a user.

The present invention utilizes a drive means connected to a motion transfer apparatus to provide movement to a plurality of massaging fingers. The drive means can include an electrical and/or battery power motor. The motion transfer apparatus can include a combination of intermeshed gears, shafts and other motion transferable components. A housing is utilized to provide protection and give an aesthetic appearance to the drive means, motion transfer apparatus and massaging fingers.

In operation, a user positions his foot within an opening contained within the housing, positioning the massaging fingers between his toes. Power is then supplied to the drive means by a power source means, such as an electrical power source. The drive means, which is engaged to the motion transfer apparatus, provides movement to the apparatus. This movement is transferred by way a series of components, such as gears and shafts, to the massaging fingers, causing the fingers to move in such a manner as to provide a massaging effect to the user.

Another embodiment of the invention envisions the device configured in such a manner as to accommodate both feet of a user in order to be massaged simultaneously.

Another embodiment of the invention envisions a device with multi-layered massaging fingers. The fingers would be positioned between and on the tops of a users toes.

Another embodiment of the invention envisions the massaging fingers to move in a piston like manner over the tops of the user's toes.

The primary object of the present invention is to provide a foot massaging device which incorporates advantages over the existing prior art.

Another object of the present invention is to provide a foot massaging device which is able to provide a massaging effect between a user's toes.

Another object of the present invention is to provide a foot massaging device which is able to simultaneously provide a massaging effect to the toes of both feet of a user.

Another object of the present invention is to provide a foot massaging device which is able to provide a massaging effect between and on top of a user's toes.

DETAILED DESCRIPTION OF THE PREFERRED EMBODIMENTS

Figure 1:
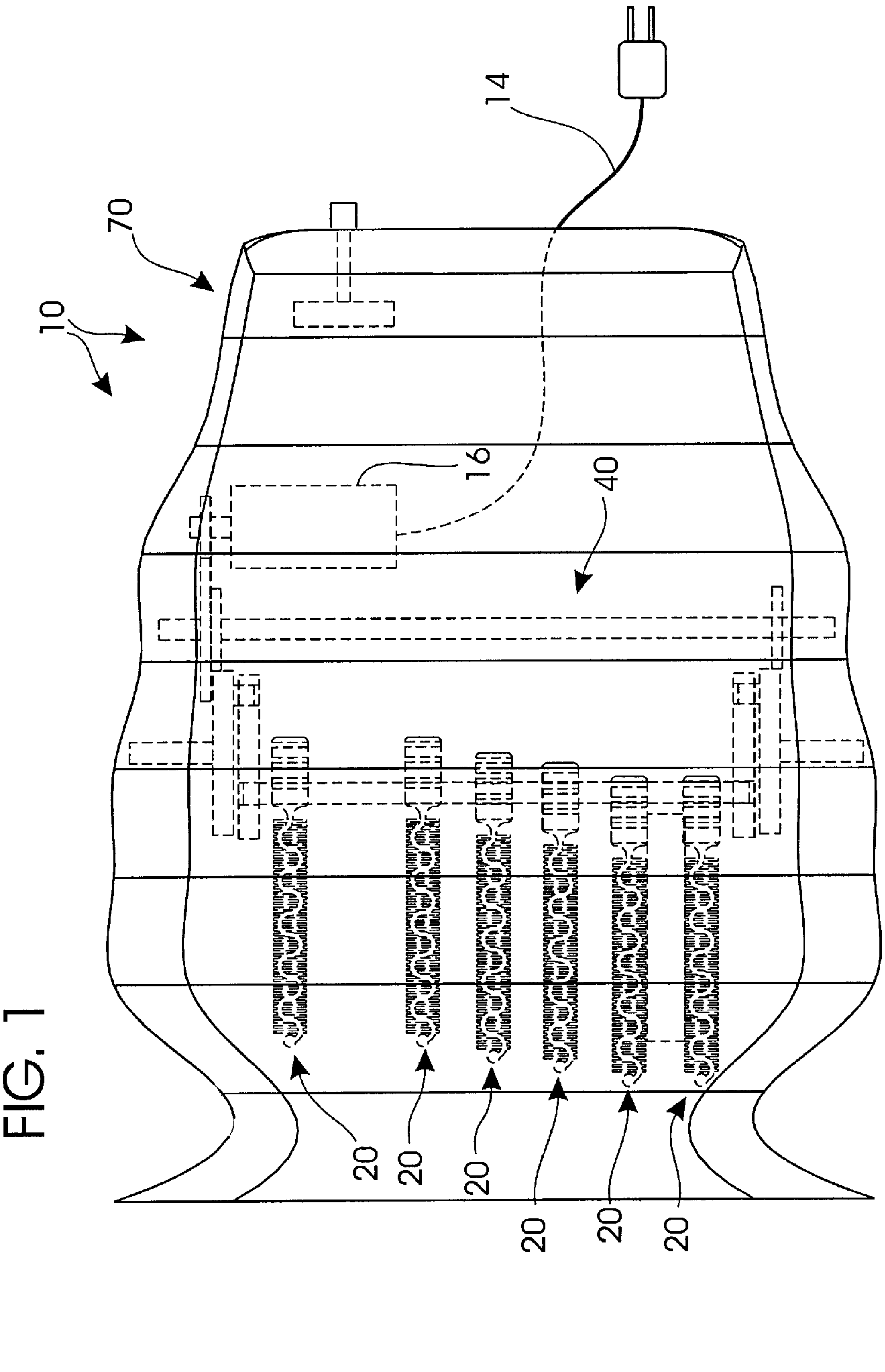
FIG. 1 shows a perspective view of the present invention.

Referring now to the figures, a foot massaging device 10 according to the present invention is shown. As generally illustrated in FIG. 1, a foot massaging device 10 having a housing 70 covering a drive means 16, a motion transfer apparatus 40 and a plurality of massaging fingers 20 is shown. Power is supplied to device 10 by a power source means 14. When power is supplied to device 10, drive means 16 provides movement to motion transfer apparatus 40 which in turn provided movement to the massaging fingers 20, causing a massaging effect upon the toes 5 of a users foot 7.

As shown in FIG. 1, power source means 14 for the preferred embodiment of the present invention is shown to be an electrical power source, such as a standard wall socket. This is merely illustrative. Other power source means which could provide power to device 10 are considered as part of the scope of the present invention.

As shown in FIG. 1, drive means 16 for the preferred embodiment of the present invention is shown to be an electrical motor. This is merely illustrative. Other drive means, such as a battery powered motor, are considered as part of the scope of the present invention.

Figure 2:
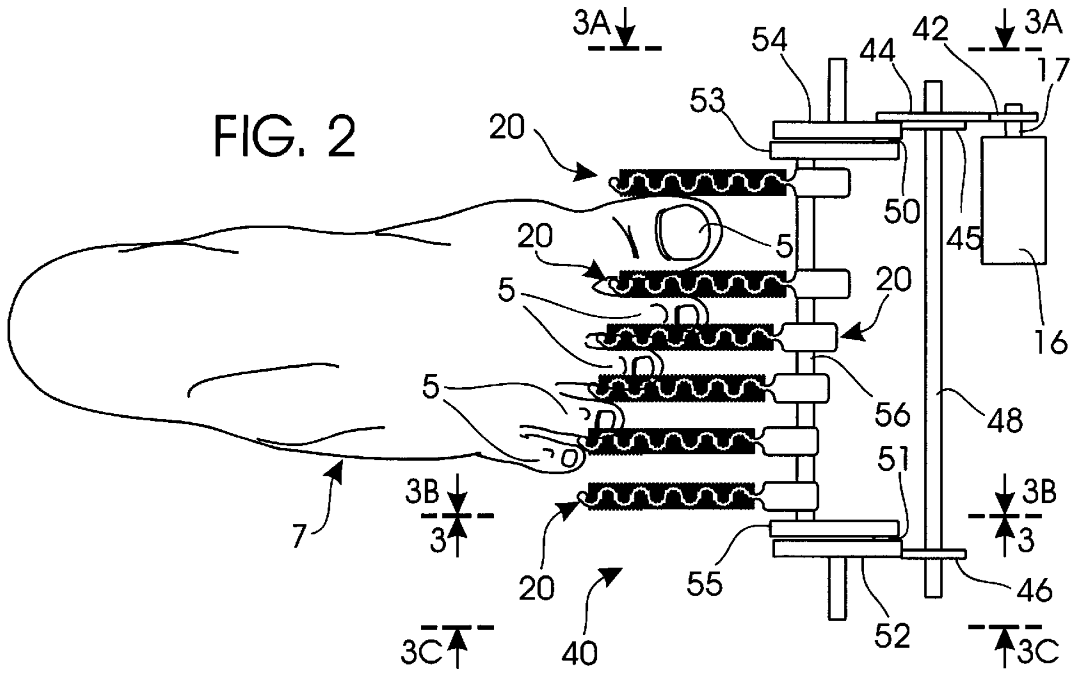
FIG. 2 shows a top view of the internal components of the present invention.
Figure 3:
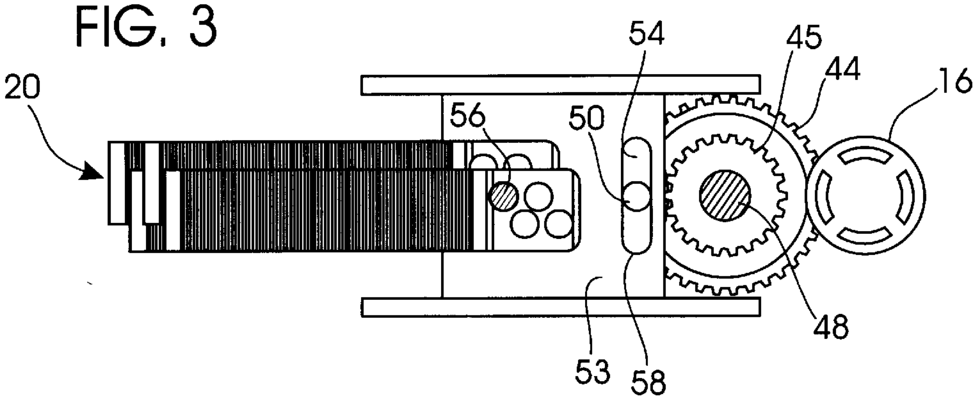
FIG. 3 shows a side view of the internal components of the present invention along line 3 as shown in FIG. 2.
Figure 3A:
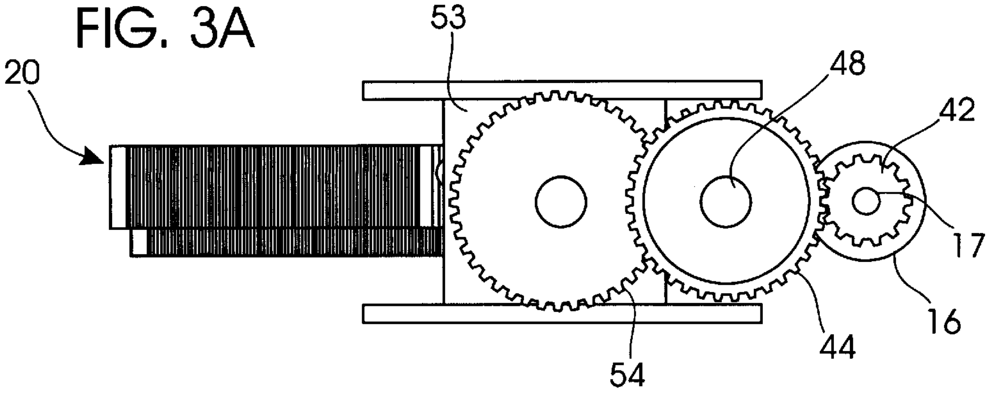
FIG. 3A shows a side view of the internal components of the present invention along line 3A as shown in FIG. 2.
Figure 3B:
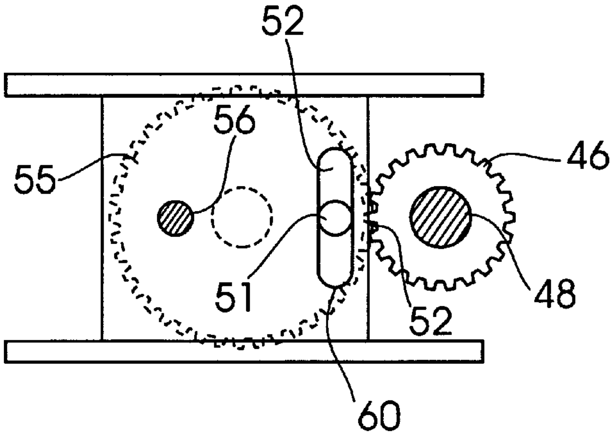
FIG. 3B shows a side view of the internal components of the present invention along line 3B as shown in FIG. 2.
Figure 3C:
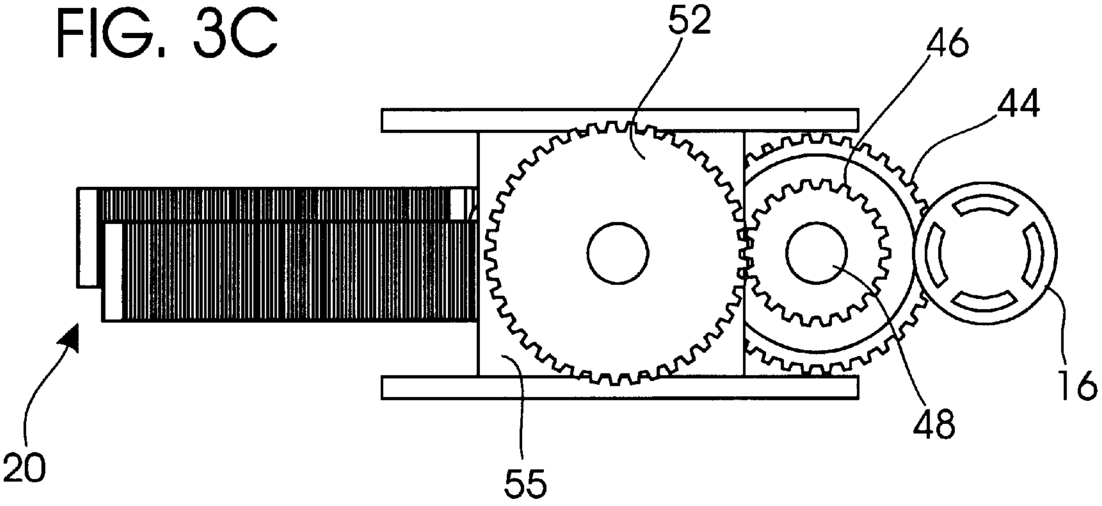
FIG. 3C shows a side view of the internal components of the present invention along line 3C as shown in FIG. 2.

As shown in FIGS. 2 and 3, motion transfer apparatus 40 generally includes a plurality of motion transfer components, such as gears and shafts. As illustrated in FIG. 2, the motion transfer apparatus 40 of the preferred embodiment of the present invention has a drive shaft 17 connected to drive means 16. A first gear 42 is connected to drive shaft 17. Second gear 44 is intermeshed with first gear 42. Connected to second gear 44 is a fourth gear 45 which is of a smaller outer diameter than second gear 44. Third gear 46 receives rotational motion from second gear 44 by first shaft 48.

A fifth gear 54 is intermeshed with the cogs of fourth gear 45. A sixth gear 52 is intermeshed with the cogs of third gear 46. Fifth gear 54 and sixth gear 52 receive rotational motion from third gear 46 and fourth gear 45 respectively.

A first idler 53, having a first slide path 58, is connected by a first slide peg 50 to fifth gear 54. A second idler 55, having a second slide path 60, is connected to sixth gear 52 by a second slide peg 51. First idler 53 and second idler 55 are connected by a second shaft 56.

Figure 4:
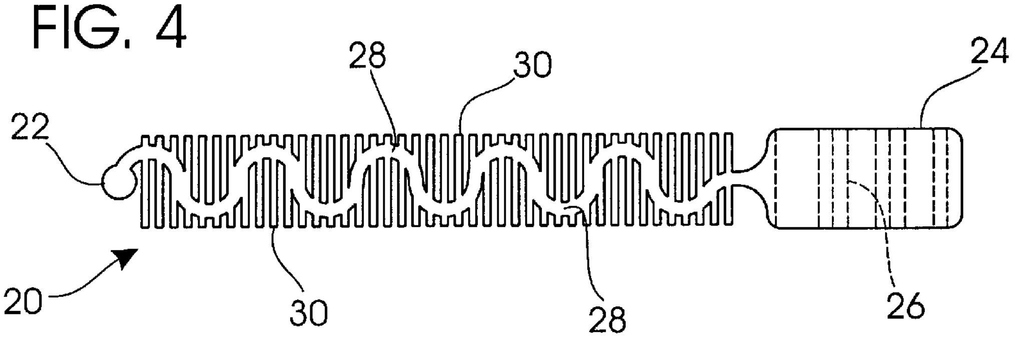
FIG. 4 shows a top view of a massaging finger component of the present invention.
Figure 5:
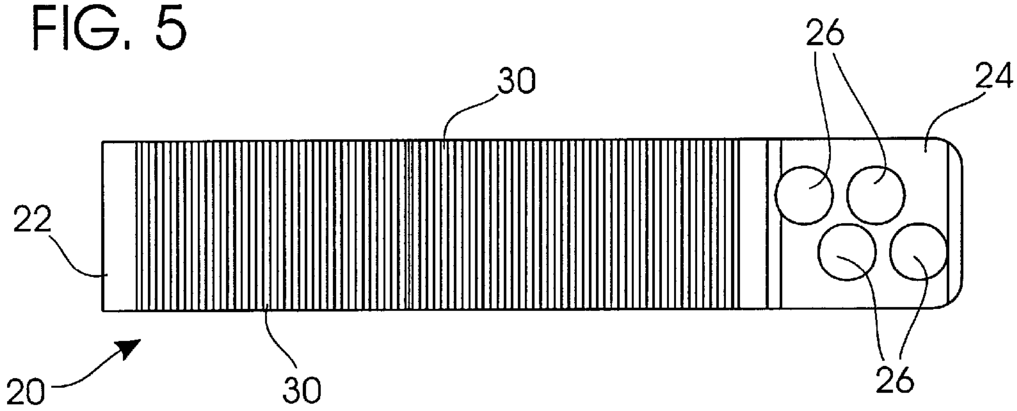
FIG. 5 shows a side view of a massaging finger component of the present invention.
Figure 6:
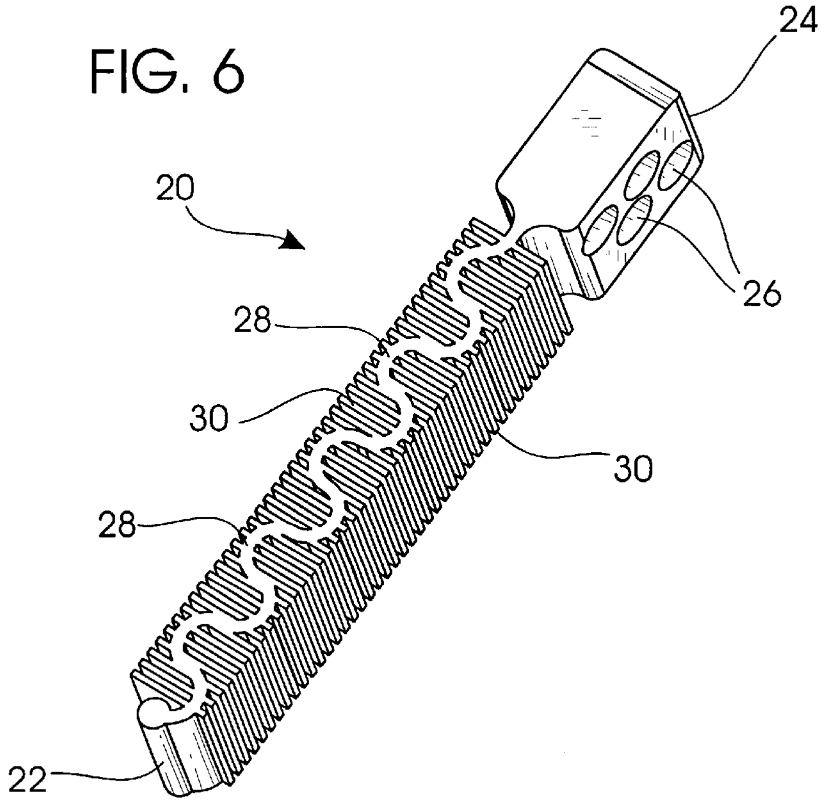
FIG. 6 shows a perspective view of a massaging finger component of the present invention.

As shown in FIGS. 4 through 6, each massaging finger 20 generally has a massaging portion 22 and a securing portion 24. Massaging portion 22 has a curved spine 28 having a sinusoidal wave shape extending from securing portion 24. Spine 28 is flexible in order to adjust to the specific foot size of the user. A plurality of brush arms 30 are secured to spine 28. The brush arms 30 are flexible and are of a variety of lengths in order to provide a variety of massaging effects.

Securing portion 24, which has a plurality of shaft adjustment holes 26, is secured to motion transfer apparatus 40. In the preferred embodiment, securing portion 24 is shown to have four shaft adjustment holes 26. This is merely illustrative. Securing portion 24 may have multiple shaft adjustment holes or a single shaft adjustment hole. As shown in FIG. 4, shaft adjustment holes 26 are offset from each other. This provides a staggered configuration in order to provide alignment with the natural curvature of a human's foot.

In the preferred embodiment, each massaging finger 20 is secured to second shaft 56 wherein second shaft 56 interfits within one of the shaft adjustment holes 26 contained within securing portion 24.

In operation, power is provided to drive means 16 by power source 14. Drive means 16 provides rotational movement to drive shaft 17. Due to the interconnection between the gears and shafts of motion transfer apparatus 40, movement is transferred from drive shaft 17 through motion transfer apparatus 40 to the plurality of massaging fingers 20 which are connected to second shaft 56. Each massaging finger 20 then moves accordingly. This movement causes friction between a user's toes and brush arms 30 of each massaging finger. This friction stimulates the user's toes in a soothing fashion causing a massaging effect.

Whereas, the present invention has been described in relation to the drawings attached hereto, it should be understood that other and further modifications, apart from those shown or suggested herein, may be made within the spirit and scope of this invention.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed:

1. A device for massaging on and between the toes of a user, wherein said device comprises:

a housing having an opening, wherein said opening is adapted to receive the foot of said user;

a drive means positioned within said housing, said drive means powered by a power source means;

a plurality of massaging elements positioned within said housing, each massaging element having a securing portion and a massaging portion, wherein said massaging portion having a flexible and sinusoidal wave shaped spine and a plurality of flexible brush arms adapted to massage between the toes of said user's foot; and a motion transfer apparatus positioned within said housing and connected to said drive means and connected to said plurality of massaging elements and for transferring movement from said drive means to said plurality of massaging elements.

2. The device of claim 1 wherein said drive means is an electric motor.

3. The device of claim 1 wherein said drive means is a battery operated motor.

4. The device of claim 1 wherein said power source means is a electrical power source.

5. The device of claim 1 wherein said motion transfer apparatus is further defined as having a drive shaft connected to said drive means, said drive shaft receiving rotational motion from said drive means, a first gear connected to said drive shaft, a second gear intermeshed with said first gear, a first shaft connected to said second gear, a third gear connected to said first shaft, a fourth gear connected to said second gear, said fourth gear positioned in line with said first shaft, a fifth gear intermeshed with said fourth gear, a sixth gear intermeshed with said third gear, a first idler having a first slide path connected by a first slide peg to said fifth gear, a second idler having a second slide path connected by a second slide peg to said sixth gear, said fifth gear, said sixth gear, said first idler and said second idler being connected in line by a second shaft, said rotational motion being transferred from said drive shaft to said fifth and said sixth gears by way of the interconnection of said first gear, second gear, third gear, fourth gear and said first shaft, said first and second idler transforming said rotational motion into translational motion by way of the interconnection between said first idler and said fifth gear and between said second idler and said sixth gear, said translational motion causing said second shaft to move along a single plane.

6. The device of claim 5 wherein said securing portion of each of said massaging elements is connected to said second shaft of said motion transfer apparatus.

7. The device of claim 1 wherein said securing portion of each of said massaging elements is further defined as having at least one shaft adjustment hole.

8. The device of claim 7 wherein of said motion transfer apparatus is further defined as having a second shaft which interfits within said shaft adjustment hole of said securing portion of each of said massaging elements.

9. A device for massaging on and between the toes of a user, wherein said device comprises:

a housing having an opening, wherein said opening receives the foot of said user;

an electric motor positioned within said housing, said electric motor powered by an electrical power source;

a plurality of massaging elements positioned within said housing, each massaging element having a securing portion and a massaging portion, wherein said massaging portion having a flexible curved spine and a plurality of flexible brush arms adapted to massage between the toes of said user's foot, said securing portion of each of said massaging elements being defined as having at least one shaft adjustment hole; and a motion transfer apparatus positioned within said housing, said motion transfer apparatus being defined as having a drive shaft connected to said electric motor, a first gear connected to said drive shaft, a second gear intermeshed with said first gear, a first shaft connected to said second gear, a third gear connected to said first shaft, a fourth gear connected to said second gear, said fourth gear positioned in line with said first shaft, a fifth gear intermeshed with said fourth gear, a sixth gear intermeshed with said third gear, a first idler having a first slide path connected by a first slide peg to said fifth gear, a second idler having a second slide path connected by a second slide peg to said sixth gear, said fifth gear, said sixth gear, said first idler and said second idler being connected in line by a second shaft, said rotational motion being transferred from said drive shaft to said fifth and said sixth gears by way of the interconnection of said first gear, second gear, third gear, fourth gear and said first shaft, said first and second idler transforming said rotational motion into translational motion by way of the interconnection between said first idler and said fifth gear and between said second idler and said sixth gear, said translational motion causing said second shaft to move along a single plane, said motion transfer apparatus being connected to said electric motor in order to receive motion from said electric motor, said motion transfer apparatus being connected to said plurality of massaging elements in order to transfer said motion to said massaging elements.

* * * * *